(12) United States Patent
Horn

(10) Patent No.: US 9,259,425 B2
(45) Date of Patent: *Feb. 16, 2016

(54) COMPOSITIONS AND METHODS FOR EYE WHITENING

(71) Applicant: Eye Therapies, LLC, Dana Point, CA (US)

(72) Inventor: Gerald Horn, Deerfield, IL (US)

(73) Assignee: Eye Therapies LLC, Dana Point, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 14/044,929

(22) Filed: Oct. 3, 2013

(65) Prior Publication Data

US 2014/0038973 A1 Feb. 6, 2014

Related U.S. Application Data

(63) Continuation of application No. 12/928,749, filed on Dec. 17, 2010.

(60) Provisional application No. 61/287,548, filed on Dec. 17, 2009.

(51) Int. Cl.
| | |
|---|---|
| *A61K 31/498* | (2006.01) |
| *A61K 9/00* | (2006.01) |
| *A61K 9/08* | (2006.01) |
| *A61K 45/06* | (2006.01) |
| *A61K 31/165* | (2006.01) |
| *A61K 31/198* | (2006.01) |
| *A61K 31/4168* | (2006.01) |
| *A61K 31/4174* | (2006.01) |
| *A61K 31/4178* | (2006.01) |

(52) U.S. Cl.
CPC ............. *A61K 31/498* (2013.01); *A61K 9/0048* (2013.01); *A61K 9/08* (2013.01); *A61K 31/165* (2013.01); *A61K 31/198* (2013.01); *A61K 31/4168* (2013.01); *A61K 31/4174* (2013.01); *A61K 31/4178* (2013.01); *A61K 45/06* (2013.01)

(58) Field of Classification Search
CPC ..................................................... A61K 31/498
USPC ......................................................... 514/249
See application file for complete search history.

(56) References Cited

U.S. PATENT DOCUMENTS

| | | | |
|---|---|---|---|
| 4,663,340 A | 5/1987 | Najer et al. | |
| 5,021,416 A | 6/1991 | Gluchowski | |
| 5,300,504 A | 4/1994 | Gluchowski | |
| 5,304,569 A | 4/1994 | Lammintausta et al. | |
| 5,424,078 A | 6/1995 | Dziabo et al. | |
| 5,561,132 A | 10/1996 | Burke et al. | |
| 5,605,911 A | 2/1997 | Olney et al. | |
| 5,677,321 A | 10/1997 | Jeon et al. | |
| 5,712,301 A | 1/1998 | Heinonen et al. | |
| 5,756,503 A | 5/1998 | Burke et al. | |
| 5,804,587 A | 9/1998 | Cupps et al. | |
| 5,914,342 A | 6/1999 | Maurer et al. | |
| 5,916,900 A | 6/1999 | Cupps et al. | |
| 5,948,804 A | 9/1999 | Jeon et al. | |
| 5,965,595 A | 10/1999 | Maurer et al. | |
| 6,040,451 A | 3/2000 | Jeon et al. | |
| 6,087,361 A | 7/2000 | Munk et al. | |
| 6,110,952 A | 8/2000 | Henry et al. | |
| 6,117,871 A | 9/2000 | Maurer et al. | |
| 6,159,998 A | 12/2000 | Jeon et al. | |
| 6,162,818 A | 12/2000 | Henry et al. | |
| 6,194,415 B1 | 2/2001 | Wheeler et al. | |
| 6,242,442 B1 | 6/2001 | Dean et al. | |
| 6,248,741 B1 | 6/2001 | Wheeler et al. | |
| 6,465,464 B2 | 10/2002 | Wheeler et al. | |
| 6,534,048 B1 | 3/2003 | Borgman | |
| 6,562,855 B1 | 5/2003 | Franks et al. | |
| 6,562,873 B2 | 5/2003 | Olejnik et al. | |
| 6,627,210 B2 | 9/2003 | Olejnik et al. | |
| 6,641,834 B2 | 11/2003 | Olejnik et al. | |
| 6,653,354 B2 | 11/2003 | Franks et al. | |
| 6,673,337 B2 | 1/2004 | Olejnik et al. | |
| 6,730,065 B1 | 5/2004 | Horn | |
| 6,916,811 B2 | 7/2005 | Boyle et al. | |
| 6,982,079 B2 | 1/2006 | Huth | |
| 7,030,149 B2 | 4/2006 | Chang et al. | |
| 7,309,706 B2 | 12/2007 | Rupp et al. | |
| 7,589,057 B2 | 9/2009 | Chang et al. | |
| 7,678,829 B2 | 3/2010 | Matier et al. | |

(Continued)

FOREIGN PATENT DOCUMENTS

| | | |
|---|---|---|
| WO | 0106347 A2 | 8/2001 |
| WO | 2009022096 A1 | 2/2009 |

(Continued)

OTHER PUBLICATIONS

Gilsbach et al., Genetic dissection of a2-adrenoceptor functions in adrenergic versus nonadrenergic cells, Molecular Phar 2009, 75(5), p. 1160-1170.

Sato et al., In Silico Functional Profiling of Small Molecules and Its Applications, Journal of Medical Chemistry 2008, 51(24), 7705-7716 (Abstract).

Lehtimaeki et al., In vitro and in vivo profiling of fadolmidine, a novel potent a2-adrenoceptor agonist with local mode of action, European Journal of Pharmacology 2008, 599(1-3), 65-71 (Abstract).

(Continued)

*Primary Examiner* — Zohreh Fay
(74) *Attorney, Agent, or Firm* — Wood, Phillips, Katz, Clark & Mortimer

(57) ABSTRACT

The invention provides compositions and methods for whitening of eyes. The provided compositions and methods utilize low concentrations of selective α-2 adrenergic receptor agonists. The compositions preferably include brimonidine.

6 Claims, 11 Drawing Sheets
(10 of 11 Drawing Sheet(s) Filed in Color)

(56) References Cited

U.S. PATENT DOCUMENTS

| | | |
|---|---|---|
| 2001/0049369 A1 | 12/2001 | Jablonski et al. |
| 2002/0156076 A1 | 10/2002 | Chow et al. |
| 2002/0197300 A1 | 12/2002 | Schultz et al. |
| 2003/0181354 A1 | 9/2003 | Abdulrazik |
| 2003/0229088 A1 | 12/2003 | Donello et al. |
| 2004/0132824 A1 | 7/2004 | Donello et al. |
| 2004/0216749 A1 | 11/2004 | Tu |
| 2004/0266776 A1 | 12/2004 | Gil et al. |
| 2005/0020600 A1 | 1/2005 | Scherer |
| 2005/0026924 A1 | 2/2005 | Graham et al. |
| 2005/0058696 A1 | 3/2005 | Donello et al. |
| 2005/0059664 A1 | 3/2005 | Gil et al. |
| 2005/0244468 A1 | 11/2005 | Huang et al. |
| 2005/0244474 A1 | 11/2005 | Huang et al. |
| 2006/0264442 A1 | 11/2006 | Ruiz et al. |
| 2007/0031472 A1 | 2/2007 | Huang et al. |
| 2007/0203085 A1 | 8/2007 | Lang |
| 2008/0020076 A1 | 1/2008 | Jhamandas et al. |
| 2008/0131483 A1 | 6/2008 | Abdulrazik |
| 2008/0131485 A1 | 6/2008 | Huang et al. |
| 2008/0207627 A1 | 8/2008 | Gil et al. |
| 2008/0207628 A1 | 8/2008 | Gil et al. |
| 2008/0233053 A1 | 9/2008 | Gross et al. |
| 2009/0176843 A1 | 7/2009 | Bhat et al. |
| 2009/0220611 A1 | 9/2009 | Castan et al. |
| 2010/0028266 A1 | 2/2010 | Horn |
| 2010/0029659 A1 | 2/2010 | Horn |
| 2010/0029661 A1 | 2/2010 | Horn |
| 2010/0029662 A1 | 2/2010 | Horn |
| 2010/0029663 A1 | 2/2010 | Horn |

FOREIGN PATENT DOCUMENTS

| | | |
|---|---|---|
| WO | 2009124755 A1 | 4/2009 |
| WO | 2010014552 A1 | 2/2010 |

OTHER PUBLICATIONS

Verbruggen et al., The effect of intravenous medetomidine on pupil size and intraocular pressure in normotensive dogs, Veterinary Quarterly 2000, 22(3), 179-180 (Abstract).

Wong et al., Design and synthesis of alpha2 adrenoceptor agonists, Book of Abstracts, 213th ACS National Meeting, San Francisco, Apr. 13-17, 1997, MEDI-023, American Chemical Society: Washington, D.C., (Abstract).

Ogidigben et al., Comparative effects of alpha-2 and DA-2 agonists on intraocular pressure in pigmented and nonpigmented rabbits, Journal of Ocular Pharmacology 1993, 9(3), 187-99 (Abstract).

Macdonald et al., Comparison of the cardiovascular effects of the a2-adrenoceptor agonist, dexmedetomidine, in rats and rabbits, Drug Development Research 1993, 28(4), 473-477 (Abstract).

Jin et al., Ocular hypotensive effects of medetomidine and its analogs, Journal of Ocular Pharmacology 1991, 7(4) 285-292 (Abstract).

Laengle et al., GLC756 decreases TNF-alpha via an alpha2 and beta2 adrenoceptor related mechanism, Experimental eye research, Nov. 2006, 83(5), 1246-1251 (Abstract).

Stamer et al., Cultured human trabecular meshwork cells express functional alpha 2A adrenergic receptors, Investigative ophthalmology & visual science Nov. 1996, 37(12), 2426-2433 (Abstract).

Pate et al., Ophthalmic arachidonylethanolamide decreases intraocular pressure in normotensive rabbits, Current eyer research Sep. 1995, 14(9), 791-797 (Abstract).

Jin et al., Ocular a2-receptor subclasses and antiglaucoma efficacy, Journal of Ocular Pharmacology, 1994, 10(1), 359-369 (Abstract).

Potter et al., Review: Alpha2 and DA2 agonists as antiglaucoma agents: Comparative pharmacology and clinical potential, Journal of Ocular Pharmacology, 1990, 6(3), 251-257 (Abstract).

Kost et al., Procedural Sedation and Analgesia in the Pediatric Emergency Department: A Review of Sedative Pharmacology, Clinical Pediatric Emergency Medicine, Dec. 2010, 11(4), 233-243 (Abstract).

Penha et al., Retinal and ocular toxicity in ocular application of drugs and chemicals—Part I: Animal models and toxicity assays, Ophthalmic Research, Jul. 2010, 44(2), 82-104 (Abstract).

Mowafi et al., Effect of dexmedetomidine premedication on the intraocular pressure changes after succinylcholine and intubation, British Journal of Anaesthesia, Apr. 2008, 100(4), 485-489.

Mowafi et al., Remifentanil obtunds intraocular pressure rises associated with suxamethonium, British Journal of Anaesthesia, Sep. 2008, 101(3), 432-433.

Bielory, Chirality in ocular agents, Current Opinion in Allergy and Clinical Immunology, Oct. 2007, 7(5), 418-423 (Abstract).

Freeman, Hypoxic-ischaemic brain injury (HIBI) after cardiopulmonary arrest, Current Anaesthesia and Critical Care, 2007, 18(5-6), 261-276 (Abstract).

Crassous et al., Interest of a2-adrenergic agonists and antagonists in clinical practice: Background, facts and perspectives, Current Topics in Medicinal Chemistry, Jan. 2007, 7(2), 187-194 (Abstract).

Gentili et al., Agonists and antagonists targeting the different a2-adrenoceptor subtypes, Current Topics in Medicinal Chemistry, Jan. 2007, 7(2), 163-186 (Abstract).

Weber et al., Neuroprotective effects of a2-adrenergic receptor agonists, Drug News and Perspectives, Apr. 2007, 20 (3), 149-154 (Abstract).

Loots, Agents for sedation in ophthalmic surgery: A review of the pharmacodynamics and clinical applications, Current Anaesthesia and Critical Care, 2006, 17(3-4), 179-190 (Abstract).

Robertson, Standing sedation and pain management for ophthalmic patients, Veterinary Clinics of North America—Equine Practice, Aug. 2004, 20(2), 485-497 (Abstract).

Ruffolo et al., a-Adrenoceptors, Pharmacology and Therapeutics, 1994, 61(1-2), 1-64 (Abstract).

Tripathi et al., Role of receptors in the trabecular meshwork of the eye as targeted to the development of antiglacoma therapy, Drug Development Research, 1992, 27(3), 1991-228 (Abstract).

Georgiou et al., Changes in NMDA receptor contribution to synaptic transmission in the brain in a rat model of glaucoma, Neurobiology of Disease, Sep. 2010, 39(3), 344-351 (Abstract).

Schoewald et al., Relationship between Steroid Permeability across Excised Rabbit Cornea and Octanol-Water Partition Coefficients, Journal of Pharmaceutical Scienses, Jun. 1978, 67(6), 786-788.

Chang et al., Improved Corneal Penetration of Timolol by Prodrugs as a Means to Reduce Systemic Drug Load, 1987, 28(3), 487-491.

Li et al., A Study of the Relationship between Cornea Permeability and Eye Irritation Using Membrance-Interaction QSAR Analysis, Toxicological Sciences, 2005, 88(2), 434-446.

Forster, et al., Adrenergic Alpha1, and Alpha2 Binding Sites are Present in Bovine Retinal Blood Vessels, Investigative Ophthalmology & Visual Science, 1987, 28(11), 1741-1746.

Donello et al., a2-Adrenoceptor Agonists Inhibit Vitreal Glutamate and Aspartate Accumulation and Preserve Retinal Function after Transient Ischemia, Journal of Pharmacology and Experimental Therapeutics, 2011, 296(1), 216-223.

Akasu et al., Reduction of the N-Type Calcuium Current by Noradrenaline in Neurones of Rabbit Vesical Parasympathetic Ganglia, Journal of Physiology, 1990, 426, 439-452.

Trendelenburg et al., a2-Adrenoceptor-mediated inhibition of cultured sympathetic neurons: changes in a2A/D-adrenoceptor-deficient mice, Naunyn-Schmiedeberg's Arch Pharmacology, 2011, 363, 110-119.

Dong et al., a2 Adrenergic Modulation of NMDA Receptor Function as a Major Mechanism of RGC Protection in Experimental Glaucoma and Retinal Excitotoxicity, Investigative Ophthalmology & Visual Science, Oct. 2008, 49(10), 4515-4522.

Saylor et al., Experimental and Clinical Evidence for Brimonidine as an Optic Nerve and REtinal Neuroprotective Agent, Arch Ophthalmol, Apr. 2009, 127(4), 402-406.

Shirasaka et al., Activation of a G Protein-coupled Inwardly Rectifying K+ Current and Suppression of Ih Contribute to Dexmedetomidine-induced Inhibition of Rat Hypothalamic Paraventricular Nucleus Neurons, Anesthesiology, 2007, 107, 605-615.

Rosa et al., Brimonidine evokes hetrogenous vasomotor response of retinal arterioles: diminished nitric oxide-mediated vasodilation when size goes small, Am J Physiol Heart Cir Physiol 2006, 291, H231-H238.

(56) References Cited

OTHER PUBLICATIONS

Wirostoko et al., The Vascular Theory in Glaucoma, Glaucoma Today, Apr. 25-27, 2009.
Huang et al., The two sides of cytokine signaling and glaucomatous optic neuropathy, j ocul biol dis inform, 2009, 2, 98-103.
Hamasaki et al., Dual a2-Adrenergic Agonist and a1-Adrenergic Antagonist Actions of Dexmedetomidine on Human Isolated Endothelium-Denuded Gastroepiploic Arteries, Anesth Analg, 2002, 94, 1434-1440.
Paris et al., The Anesthetic Effects of Etomidate: Species-Specific Interaction with a2-Adrenoceptors, Anesth Analg. 2007, 105(6), 1644-1649.
Pertovaara, Antinociceptive Properties of Fadolmidine (MPV-24-26), a Novel a2-Adrenoceptor Agonist, CNS Drug Reviews, 2004, 10(2), 117-126.
Niemi et al., Synthesis, hydrolysis, and intraocular pressure lowering effects of fadolmidine prodrugs, International Journal of Pharmaceutics 2005, 29, 121-127.
Vaidyanathan S. et al., Fluticasone Reverses Oxymetazoline-induced Tachyphylaxis of Response and Rebound Congestion, American Journal of Respiratory and Critical Care Medicine vol. 182, 19-24, 2010.
AFT Pharmaceuticals Ltd., Brimonidine AFT. 2005; p. 1, para 2-3, 5 http://www.medsafe.govt.nz/Profs/Datasheet/b/Brimonidine-AFTeyedrops.pdf.
Mechanism of decongestant activity of x2-adrenoceptor agnosits, CORBOZ M.R. et al., Pulmonary Pharmacology & Therapeutics 21 (2008) 449-454.
Alpha-adrenoceptor agonistic activity of oxymetazoline and xylometazoline, Haenisch B. et al., Fundam Clin Pharmacol. Dec. 17, 2009.
An Evaluation of Nasal Response Following Different Treatment Regimes of . . . , Morris S. et al., American Journal Rhinology, vol. 11, No. 2, Mar.-Apr. 1997, pp. 109-115.
Pharmacological Characterization of Postjunctional a-Adrenoceptors in . . . , Corboz M.R. et al., American Jour of Rhinology, vol. 19, No. 5, Sep.-Oct. 2005, pp. 495-502.
Postjuntional a2-adrenoceptors in blood ve3ssels of human nasal mucosa, Ichimura K. et al., Arch Otorhinolaryngol (1988) 245:127-131.
Long-term use of oxy- and xylometazoline nasal sprays induces rebound swelling, tolerance, and nasal hyperreactivity, GRAF P., Rhinology 1996, 34(1):9-13.
Alpha 1-receptors at pre-capillary resistance vessels of the human nasal mucosa, Johannssen V et al., Rhinology 1997; 35(4):161-65.
Correspondence A Propos De L'article: <<Traitement Des Glaucomes Par La Brimonidine>>, M. Detry-Morel Et C. Dutrieux< J Fr Ophtalmol.2001; 24(7): 748-9.
Potent a2A-Adrenoceptor-Mediated Vacoconstriction by Brimonidine in Porcine Ciliary Arteries, Anna Wikberg-Matsson, et al., IOVS, 2001, vol. 42, No. 9, 2049-55.
Medical Management of Chronic Rhinosinusitus—Jean P. Fong, MD, Matthew Ryan, MD (May 2006).
Prevent Drugs from Going Missing in Action—Mark B. Abelson, MD, and Sarah A. Rosner MPH; Review of Opthalmology; www.revophth.com/index.asp?page1_357.htm.
Interactions Between CA2+ and H+ and Functional Consequences in Vascular Smooth Muscle—C. Austin and S. Wray, Journ. of Amer. Heart Association (Circ. Res. 2000; 86:355-363).
A Useful New Topical Treatment for Glaucoma and Ocular Hypertension—Drug Ther Perspect 13(1):1-4, 1999.
Vartiainen, J, Dexmedetomidine-Induced Ocular Hyptension in rabbits with normal or elevated intraocular pressures, Invest. Ophthalmol. Vis. Sci. May 1992, 33(6), 2019-2023.
Silent Bedpartners—Nancy A. Collop, Chest 2002; 122, 1111-1112.
Traitment Des Glaucomes Par La Briminodine (Alphagan 0.2%)—M. Detry-Morel, C. Dutrieux, J. Fr. Opthamol., 2000; 23, 8, 763-768.
Vasopressin-Induced Vasoconstriction; Two Concentration-Dependen Signaling Pathways—Kyle K. Henderson and Kenneth L. Bryon, J. Appl. Physiol. 102: 1402-1409, 2007.
The Effect of Correction of Sleep-Disordered Breathing on Bp in Untreated Hypertension—K. Mae Hla, J.B. Skatrud, L. Finn, M. Palta and T. Young, Chest 2002:122 1125-1135.
Myogenic Tone and Reactivity of the Rat Opthalmic Artery—Y.P.R. Jarajapu, M.B. Grant, and H.J. Knot Invest. Opth. & Visual Science, Jan. 2004, vol. 45, No. 1.
Munoz, G, et al., Increased risk for flap dislocation with perioperative brimonidine use in femtosecond laser in situ keratomileusis, J Cataract Refact Surg 2009, 35, 1338-1342.
Prospective Study of the Association Between Sleep-Disordered Breathing and Hypertension—P. Peppard, et. al., The New England J. of Med, vol. 342, No. 19:1378:1384 (2000).
Catecholemnines and Sympathomimetic Drugs—Goodman & Gilman's Pharmacology, Ch. 10; www.accessmedicine.com/popup.aspx?aID-936314&pring=yes_chapter.
Rhinitis Medicamentosa—JT Ramey, E Bailen, RF LOckey, J. Investig. Allergol. Clin. Immunol. 2006; vol. 16(3); 148-155.
Characterization of three inhibitors of endothelial nitric oxide synthase in vitro and in vivo—D.D> Rees, et al., br. J. Pharmacol. (1990) 101, 746-752.
Inhibition of a-adrenergic vasoconstriction in exercising human thigh muscles—D. Walter Wray, et al., J. Physiol. 555, 2 pp. 545-564 (2003).
Dexmedetomidine Enhances the Local Anesthetic Action of Lidocaine via . . . Tatsushi Yoshitomi DDS et al., Anesth. Analg. 2008I 107:96-101.
Adding Dexmedetomidine to Lidocaines for Intravenous Regional Anesthesia, Dilek Memis, MS et. al, Anesth. Analg. 2004:98:835-40.
Hardman et al., Goodman and Gilman's the pharmacological basis of therapeutics: 10th edition, Aug. 28, 2001, p. 3-29, McGraw-Hill Professional.
Cantor, Louis B., Brimonidine in the treatment of glaucoma and ocular hypertension, Ther. Clin. Risk Manag., Dec. 2006, 2(4), 337-346.
Hong S., et al., Effect of prophylactic brimonidine instillation on bleeding during strabismus surgery in adults, Am J Ophthalmol, Sep. 2007, 144(3), 469-470.
Drugs.com: Apraclonidine, 2015, at http://www.drugs.com/ppa/apraclonidine-hydrochloride.html?printable=1.
NDA 21-764/S-005 Qoliana(R), 2012, at http://www.accessdata.fda.gov/drugsatfda_docs/label/2012/021764s005lbl.pdf.
Cantor, L.B., Brimonidine in the treatment of glaucoma and ocular hypertension, Ther Clin Risk Manag, Dec. 2006, 2(4), 337-48.
Saxena, S., et al., Pharmacotherapy of glaucoma, Indian J Pharma, Apr. 2002, 34(2), 71-85.
In re Brimonidine Patent Litigation, 643 F.3d 1366 (Fed. Cir. 2011).

FIG. 4b          FIG. 4c          FIG. 4d

COMPOSITIONS AND METHODS FOR EYE WHITENING

BACKGROUND OF THE INVENTION

Adrenergic receptors mediate physiological responses to the catecholamines, norepinephrine and epinephrine, and are members of the superfamily of G protein-coupled receptors having seven transmembrane domains.

These receptors, which are divided pharmacologically into α-1, α-2 and β-adrenergic receptor types, are involved in diverse physiological functions including functions of the cardiovascular and central nervous systems. The α-adrenergic receptors mediate excitatory and inhibitory functions: α-1 adrenergic receptors are typically excitatory post-synaptic receptors which generally mediate responses in an effector organ, while α-2 adrenergic receptors are located postsynaptically as well as presynaptically, where they inhibit release of neurotransmitters. The α-adrenergic receptors also mediate vascular constriction.

α-2 adrenergic receptors are presently classified into three subtypes based on their pharmacological and molecular characterization: α-2A/D (α-2A in human and α-2D in rat); α-2B; and α-2C (Bylund et al., Pharmacol. Rev. 46:121-136 (1994); and Hein and Kobilka, Neuropharmacol. 34:357-366 (1995)). The α-2A, α-2B, and α-2C subtypes appear to regulate arterial and/or venular contraction in some vascular beds, and the α-2A and α-2C subtypes also mediate feedback inhibition of norepinephrine release from sympathetic nerve endings.

A human eye has a lot of α-2 adrenergic receptors. Agonists of these receptors may have an effect on an eye's appearance by causing lumen size reduction of α-2 receptor populated arterioles and, particularly, terminal arterioles. This may result in vasoconstriction, and more particularly microvessel lumen size reduction, which in turn may increase the per unit surface area degree of microvessel constriction, and therefore, improve cosmetic appearance of eyes. Whiter eyes are traditionally a societal symbol of natural healthy eyes, and excellent overall hygiene and health.

While some compounds may be agonists of both α-1 and α-2 receptors, there are many compounds which have selective α-2 agonist activity, meaning that they preferentially bind to α-2 adrenergic receptors. They include brimonidine (which has been used for lowering intraocular pressure in patients with open-angle glaucoma or ocular hypertension), guanfacine (which has been used to control high blood pressure), dexmedetomidine (which has been used as a sedative, analgesic, sympatholytic and anxiolytic), and methyl dopa (which has been used as a centrally acting adrenergic antihypertensive).

However, selective α-2 adrenergic receptor agonists, when used at conventional doses of 0.1% or higher, are associated with a number of undesirable side effects, such as rebound hyperemia. These effects may be associated with a "crossover" stimulation of α-1 adrenergic receptors, as α-2 selectivity is a ratio of α-2/α-1 receptor activity.

Thus, there is a need for new compositions and methods that would improve cosmetic appearance of eyes by achieving eye whitening with reduced or eliminated side effects.

SUMMARY OF THE PRESENT INVENTION

The present invention provides compositions and methods for achieving cosmetic eye whitening which utilize low concentrations of selective α-2 adrenergic receptor agonists.

In some embodiments of the invention, the selective α-2 adrenergic receptor agonists have binding affinities (K) for α-2 over α-1 receptors of 100:1 or greater. In preferred embodiments of the invention, the selective α-2 adrenergic receptor agonists have $K_i$ for α-2 over α-1 receptors of 300:1 or greater, more preferably 500:1 or greater, more preferably 700:1 or greater, even more preferably 1000:1 or greater, and most preferably, 1500:1 or greater.

In preferred embodiments of the invention, concentrations of the selective α-2 adrenergic receptor agonists are from about 0.0001% to about 0.05%; more preferably, from about 0.001% to about 0.025%; even more preferably, from about 0.01% to about 0.025%; and even more preferably, from about 0.01% to about 0.02% weight by volume of the composition.

In preferred embodiments of the invention, the selective α-2 adrenergic receptor agonist is selected from the group consisting of apraclonidine, mivazerol, clonidine, brimonidine, alpha methyl dopa, guanfacine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds.

The compositions and methods of the invention may be used to whiten healthy eyes and/or to reduce hyperemia in an eye which is due to a disease or a condition.

The reduction in redness and additional increase in whiteness can be measured on one of the following scales, such as the McMonnies/Chapman-Davies scale (MC-D); the Institute for Eye Research scale (IER, previously known as CCLRU scale); the Efron scale; and a validated bulbar redness scale (VBR) developed at the Centre for Contact Lens Research. (*The Use of Fractal Analysis and Photometry to Estimate the Accuracy of Bulbar Redness Grading Scales*, Marc M. Schulze et al, Investigative Ophthalmology and Visual Science, 2008; 49:1398-1406). Alternatively, the invention also describes a modified scale that can more accurately measure the reduction in redness and the additional increase in whiteness.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIGS. 4B-4D are photographs of eyes of healthy individuals;

DETAILED DESCRIPTION OF THE INVENTION

Definitions

Figure 1:
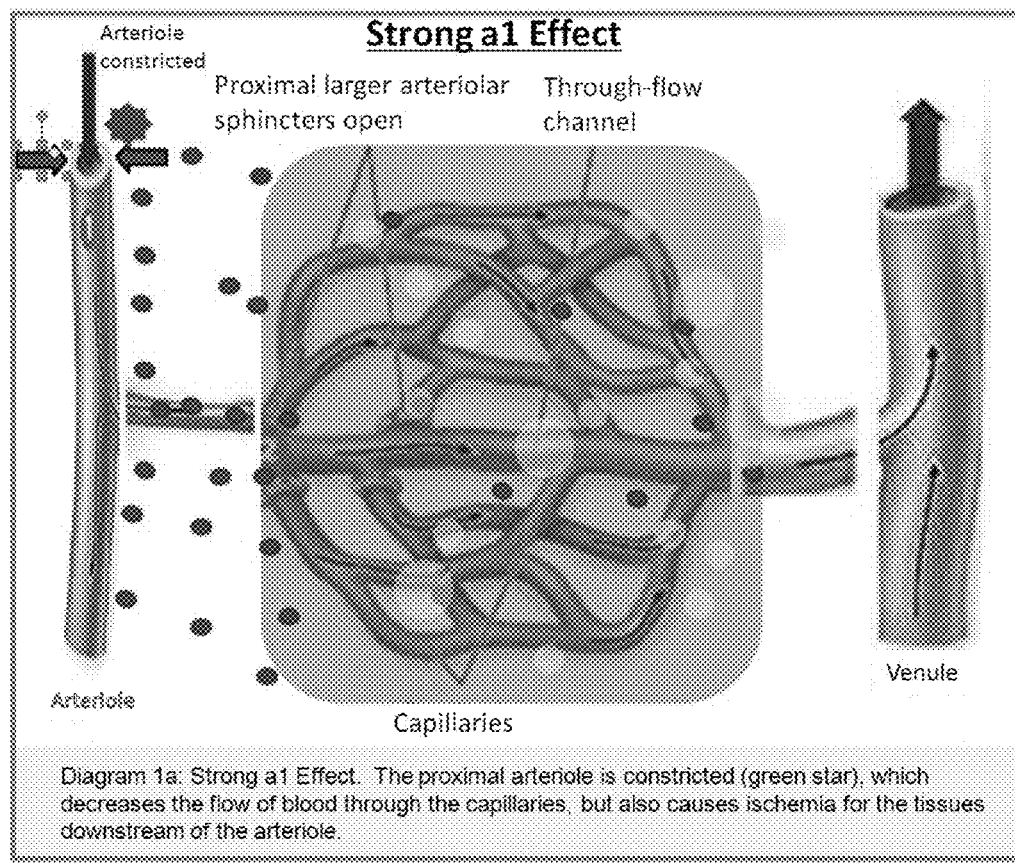
FIG. 1 is a graphical representation of the effects of activating α-1 adrenergic receptors.

For purposes of the present invention, the terms below are defined as follows.

The term "selective α-2 adrenergic receptor agonists" encompasses all α-2 adrenergic receptor agonists which have a binding affinity of 100 fold or greater for α-2 over α-1 adrenergic receptors.

The term "low concentrations" refers to concentrations from between about 0.0001% to about 0.05%; more preferably, from about 0.001% to about 0.025%; even more preferably, from about 0.01% to about 0.025%; and even more preferably, from about 0.01% to about 0.02% weight by volume of the composition.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, Alphagan™, and UK14304.

As used herein, the term "composition" is intended to encompass a product comprising the specified ingredients in the specified amounts, as well as any product which results, directly or indirectly, from a combination of the specified ingredients in the specified amounts.

EMBODIMENTS OF THE INVENTION

It was surprisingly and unexpectedly found that selective alpha-2 (α-2) adrenergic receptor agonists (which are interchangeably referred to as "α-2 agonists" throughout the application) at sufficiently low concentrations allow significant improvement in tissue hemodynamics and can be used for cosmetic whitening of eyes with reduced or eliminated side effects.

Thus, in one aspect, the invention provides compositions and methods to increase whiteness of an eye. In one embodiment, the invention provides methods and compositions for achieving eye whitening in healthy eyes, above and beyond reduction of hyperemia due to a disease or a condition.

The presently claimed methods and compositions can increase whiteness of an eye several shades beyond the baseline of a particular eye. This increase in whiteness may be important for cosmetic or other reasons. A normal healthy eye has a certain baseline level of whiteness, which slightly varies from person to person. The reduced whiteness of the sclera is often viewed as cosmetically less desirable, and may be an indicator of fatigue, lack of sleep, lack of sobriety, drug use, emotional lability, and overall poor health. Whiter sclera is often viewed as more cosmetically desirable, associated with improved hygiene and/or health, and a cleaner, healthier lifestyle.

Not wishing to be bound to a specific theory, the present invention may accomplish this additional whitening through microvascular vasoconstriction of the vessels and, particularly, microvessels of the white layer of the eye (i.e., the sclera). In addition, compositions and methods of the present invention may affect vasoconstriction of overlying episcleral and/or conjunctival tissue microvessels which may also be involved in the whitening of an eye. This effect is believed to be similar to teeth whitening, where grading scale quantification includes improvement relative to an estimated baseline, where whitening beyond baseline is referred to as "bleaching."

Selective α-2 Adrenergic Receptor Agonists Suitable for the Purposes of the Invention In some embodiments of the invention, selective α-2 adrenergic receptor agonists have binding affinities (K) for α-2 over α-1 receptors of 100:1 or greater. In preferred embodiments of the invention, selective α-2 adrenergic receptor agonists have $K_i$ for α-2 over α-1 receptors of 300:1 or greater, more preferably 500:1 or greater, more preferably 700:1 or greater, even more preferably 1000:1 or greater, and most preferably, 1500:1 or greater. Generally, a selective α-2 adrenergic receptor agonist which has $K_i$ for α-2 over α-1 receptors greater than that of oxymetazoline should be suitable for the purposes of the invention.

It is well within a skill in the art to design an assay to determine α-2/α-1 functional selectivity. As non-limiting examples, potency, activity or $EC_{50}$ at an α-2A receptor can be determined by assaying for inhibition of adenylate cyclase activity. Furthermore, inhibition of adenylate cyclase activity can be assayed, without limitation, in PC12 cells stably expressing an α-2A receptor such as a human α-2A receptor. As further non-limiting examples, potency, activity or $EC_{50}$ at an α-1A receptor can be determined by assaying for intracellular calcium. Intracellular calcium can be assayed, without limitation, in HEK293 cells stably expressing an α-1A receptor, such as a bovine α-1A receptor.

Not desiring to be bound by any specific theory or mechanism, it is believed that the particularly preferred adrenergic receptor agonists for the purposes of the present invention have higher selectivity for α-2B and/or α-2C receptors, as compared to α-2A receptors.

In preferred embodiments of the invention, concentrations of selective α-2 adrenergic receptor agonists are from about 0.0001% to about 0.05%; more preferably, from about 0.001% to about 0.025%; even more preferably, from about 0.01% to about 0.025%; and even more preferably, from about 0.01% to about 0.02% weight by volume of the composition.

Any selective α-2 adrenergic receptor agonist may be suitable for the purposes of the present invention. In one embodiment, the selective α-2 adrenergic receptor is selected from the group consisting of apraclonidine, mivazerol, clonidine, brimonidine, alpha methyl dopa, guanfacine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds.

Compositions and methods of the inventions encompass all isomeric forms of the described α-2 adrenergic receptor agonists, their racemic mixtures, enol forms, solvated and unsolvated forms, analogs, prodrugs, derivatives, including but not limited to esters and ethers, and pharmaceutically acceptable salts, including acid addition salts. Examples of suitable acids for salt formation are hydrochloric, sulfuric, phosphoric, acetic, citric, oxalic, malonic, salicylic, malic, fumaric, succinic, ascorbic, maleic, methanesulfonic, tartaric, and other mineral carboxylic acids well known to those in the art. The salts may be prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference).

As long as a particular isomer, salt, analog, prodrug or other derivative of a selective α-2 adrenergic receptor agonist functions as a highly selective α-2 agonist, it may be used for the purposes of the present invention.

When choosing a particular α-2 adrenergic receptor agonist, one may take into account various considerations including blood brain permeability and any possible side effects and other systemic reactions.

In preferred embodiments of the invention, the selective α-2 adrenergic receptor is brimonidine or its salt. In a more preferred embodiment, the selective α-2 adrenergic receptor agonist is the tartrate salt of brimonidine.

Compositions and Methods of the Invention

In one embodiment, the invention provides a composition comprising a low dose of a selective α-2 adrenergic receptor agonist, or a pharmaceutically acceptable salt thereof, for use in increasing whiteness of an eye.

In a preferred embodiment, the selective α-2 adrenergic receptor agonist is present at a concentration below about 0.05% weight by volume, and more preferably, between about 0.001% to about 0.05% weight by volume.

The concentration of the selective α-2 adrenergic receptor agonist is preferably below the concentration at which α-1 adrenergic receptors are sufficiently activated to cause adverse ischemic vasoconstrictive consequences.

In one embodiment, the selective α-2 adrenergic receptor agonist is selected from the group consisting of lofexidine, apraclonidine, mivazerol, clonidine, brimonidine, alpha methyl dopa, guanfacine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds.

In a preferred embodiment, the composition comprises brimonidine at a concentration between about 0.001% and about 0.025% weight by volume.

In a more preferred embodiment, a pH of the composition comprising the selective α-2 adrenergic receptor agonist is between about 5.5 and about 6.5.

In one embodiment, the invention provides an aqueous composition for use in increasing whiteness of an eye, consisting essentially of brimonidine, wherein brimonidine concentration is from between about 0.01% to about 0.025% weight by volume, wherein pH of said composition is between about 5.5 and about 6.5.

In a preferred embodiment, the invention provides an aqueous composition for use in increasing whiteness of an eye, comprising between about 0.01% to about 0.025% weight by volume of brimonidine and from between about 0.1 to about 0.5% weight by volume of potassium chloride, wherein pH of said composition is between about 7.0 and about 8.0, and wherein said composition is formulated for a topical administration.

The compositions of the present invention are preferably formulated for a mammal, and more preferably, for a human.

In one embodiment, a pH of the compositions of the present invention is less than about 8.0, preferably, between about 5.5 and about 8.0, more preferably between about 6.0 and about 8.0.

In another preferred embodiment, the compositions of the present invention further include potassium (i.e., $K^+$). The term "potassium" includes, but is not limited to, potassium salt. In a preferred embodiment, potassium is in the form of potassium chloride (KCl) and its concentration is between about 0.2% to about 0.9% weight by volume.

In another preferred embodiment, the compositions of the present invention further include calcium (i.e., $Ca^{2+}$). The term "calcium" includes, but is not limited to, calcium salt. Preferably, calcium is calcium chloride ($CaCl_2$).

In a more preferred embodiment, the selective α-2 adrenergic receptor has KCl in a concentration range of 0.1%-0.8% weight by volume, preferably 0.25% weight by volume. The higher concentration of KCl may contribute to a more prolonged duration of action of compositions of the invention.

In a still more preferred embodiment, the compositions of the invention may have pH of above 7.0 and KCl of 0.1%-0.8% weight by volume.

In a still more preferred embodiment, the compositions of the invention may have a pH of above 7.0 and KCl of 0.1%-0.8% and $CaCl_2$ above 0.01% weight by volume.

In another preferred embodiment, the compositions of the invention also comprise a solubility stabilizer which preferably contains an anionic component, such as peroxide class preservatives. The solubility stabilizer allows one to achieve greater penetration of lipophilic membranes. In a preferred embodiment, the solubility stabilizer comprises a stabilized oxychloro complex, chlorite, and sodium perborate.

In yet another preferred embodiment, the compositions of the present invention comprise nitrous oxide inhibitors. In a preferred embodiment, the nitrous oxide inhibitors are selected from the group consisting of L-NAME (L-$N^G$-Nitroarginine methyl ester), L-NIL (N-6-(1-Iminoethyl)-L-lysine dihydrochloride), L-NIO (N-5-(1-Iminoethyl)-L-ornithine dihydrochloride), and L-canavine, or combinations thereof. Preferably, concentration of the nitrous oxide inhibitors is between about 0.005% and about 0.5% weight by volume.

In one embodiment of the invention, the compositions are delivered as ophthalmic solutions into the eyes. The invention also contemplates topical compositions which include, but are not limited to, gels and creams. They may also include additional non-therapeutic components, which include, but are not limited to, preservatives, delivery vehicles, tonicity adjustors, buffers, pH adjustors, antioxidants, and water.

Preservatives include, but are not limited to, benzalkonium chloride, chlorobutanol, thimerosal, phenylmercuric acetate, or phenylmercuric nitrate.

Delivery vehicles include, but are not limited to, polyvinyl alcohol, povidone, hydroxypropyl methyl cellulose, poloxamers, carboxymethyl cellulose, hydroxyethyl cellulose and purified water. It is also possible to use a physiological saline solution as a major vehicle.

Tonicity adjustors include, but are not limited to, a salt such as sodium chloride, potassium chloride, mannitol or glycerin, or another pharmaceutically or ophthalmically acceptable tonicity adjustor.

Buffers and pH adjustors include, but are not limited to, acetate buffers, citrate buffers, phosphate buffers and borate buffers. It is understood that acids or bases can be used to adjust the pH of the composition as needed.

Antioxidants include, but are not limited to, sodium metabisulfite, sodium thiosulfate, acetylcysteine, butylated hydroxyanisole and butylated hydroxytoluene.

To make the topical compositions of the present invention, one can simply dilute, using methods known in the art, more concentrated solutions of selective α-2 agonists. The precise method of carrying out the dilutions is not critical. Any commonly used diluents, including preservatives described above in the application, suitable for topical solutions can be used.

In other embodiments, the compositions of the invention may be formulated and delivered as intravenous, oral, aerosolized, and nebulized compositions.

Dosages

Proper dosages of the compositions of the present invention are concentration-dependent. To determine the specific dose for whitening of eyes of a specific person, a skilled artisan would have to take into account kinetics and absorption characteristics of the particular selective α-2 adrenergic receptor agonist. In addition, the dosage may be dependent on the route of administration. The dosages may also de dependent on the degree of whitening desired by a patient.

The present invention is more fully demonstrated by reference to the accompanying drawings.

FIG. 1 is a graphical representation of the effects of activating α-1 adrenergic receptors. As FIG. 1 demonstrates, administering α-1 adrenergic receptor agonists leads to constriction of the proximal arteriole (on the left side of FIG. 1) which in turn decreases the flow of blood through the capillaries and causes ischemia for the tissues downstream of the constricted arteriole.

Figure 2:
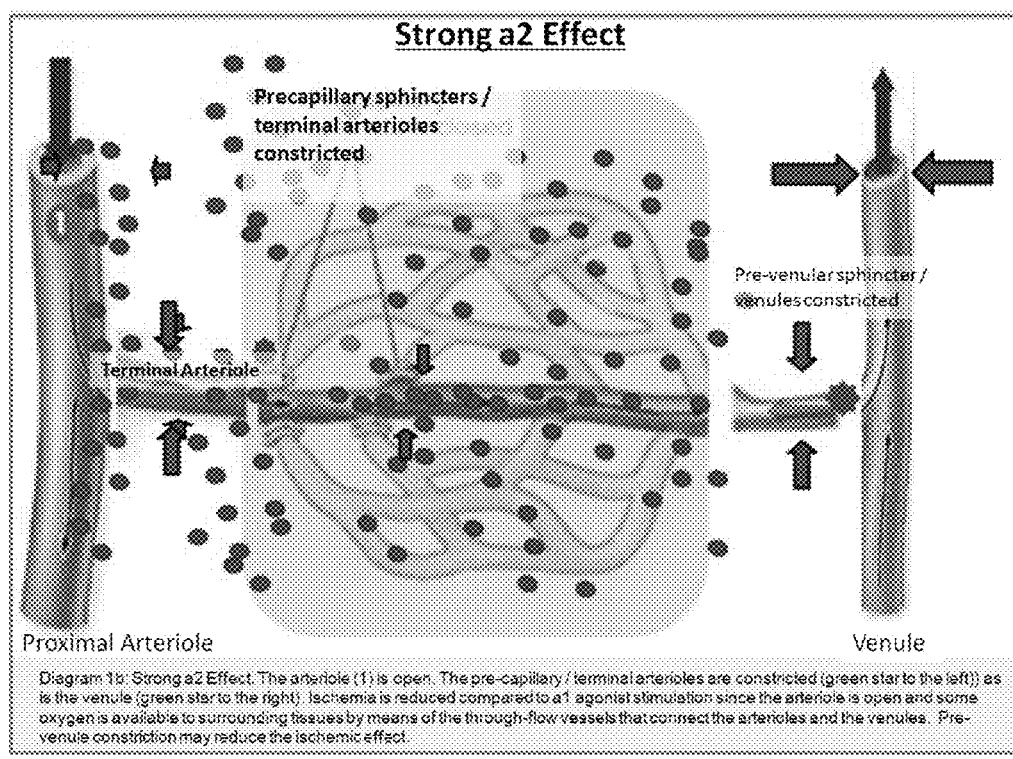
FIG. 2 is a graphical representation of the effects of preferentially activating α-2 adrenergic receptors.

FIG. 2 is a graphical representation of the effects of preferentially activating α-2 adrenergic receptors. As FIG. 2 demonstrates, administering α-2 adrenergic receptor agonists leads to constriction of the pre-capillary/terminal arteriole (i.e. smaller blood vessel) (on the left side of FIG. 1) and constriction of the venule (on the right side of FIG. 2). Ischemia is decreased, as compared to stimulating α-1 adrenergic receptors, because the arteriole is open and some oxygen is available to surrounding tissues by means of the through-flow vessels that connect the arterioles and the venules.

Figure 3:
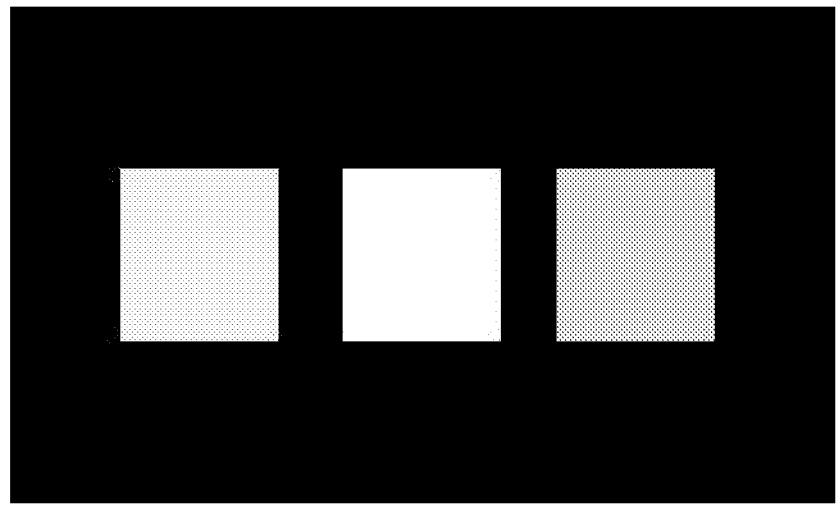
FIG. 3 is a visual representation of three different shades of whiteness.

FIG. 3 is a visual representation of three different shades of whiteness. The human eye has a limit to its ability to discriminate shades of whiteness change. The central square is set to RGB (255 255 255). The RGB color model is an additive color model in which red, green, and blue light are added together in various ways to reproduce a broad array of colors. A color in the RGB color model is described by indicating how much of each of the red, green, and blue is included. The color is expressed as an RGB triplet (rgb), each component of which can vary from zero to a defined maximum value. If all the components are at zero, the result is black; if all are at maximum, the result is the fully saturated white. RGB (255 255 255) represents the fully saturated white.

In the right square, the whiteness has been reduced by 5, based on a 1 to 100 blackness scale, where the background is 100. On the square to the left, the whiteness has been reduced by 15. The shade differential resulting from reduction by 5 is just above the threshold increment of difference in whitening detectable by most humans with normal healthy eyes.

Figure 4A:
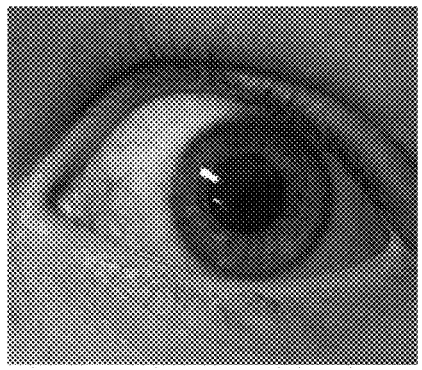
FIG. 4A is a photograph of an eye of a patient with hyperemia.
Figure 4A:
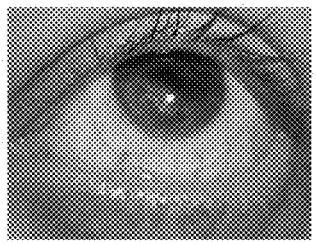
Figure 4A:
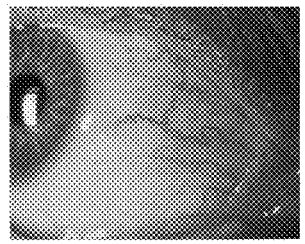
Figure 4A:
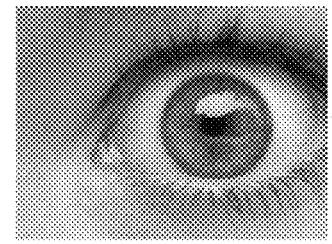

FIG. 4a is a photograph of an eye of a patient with hyperemia. Hyperemia (dilation of vessels of the conjunctiva, and less frequently underlying episclera and/or sclera) masks the whiteness of the sclera and is a common cause of increased eye redness and reduced eye whiteness. It results in the classic "red eye". However, on a more fundamental physiological level, whiteness of the sclera varies from individual to individual, even in the absence of pathology. This is demonstrated by FIGS. 4b-4d which are photographs of eyes of healthy individuals.

Figure 5:
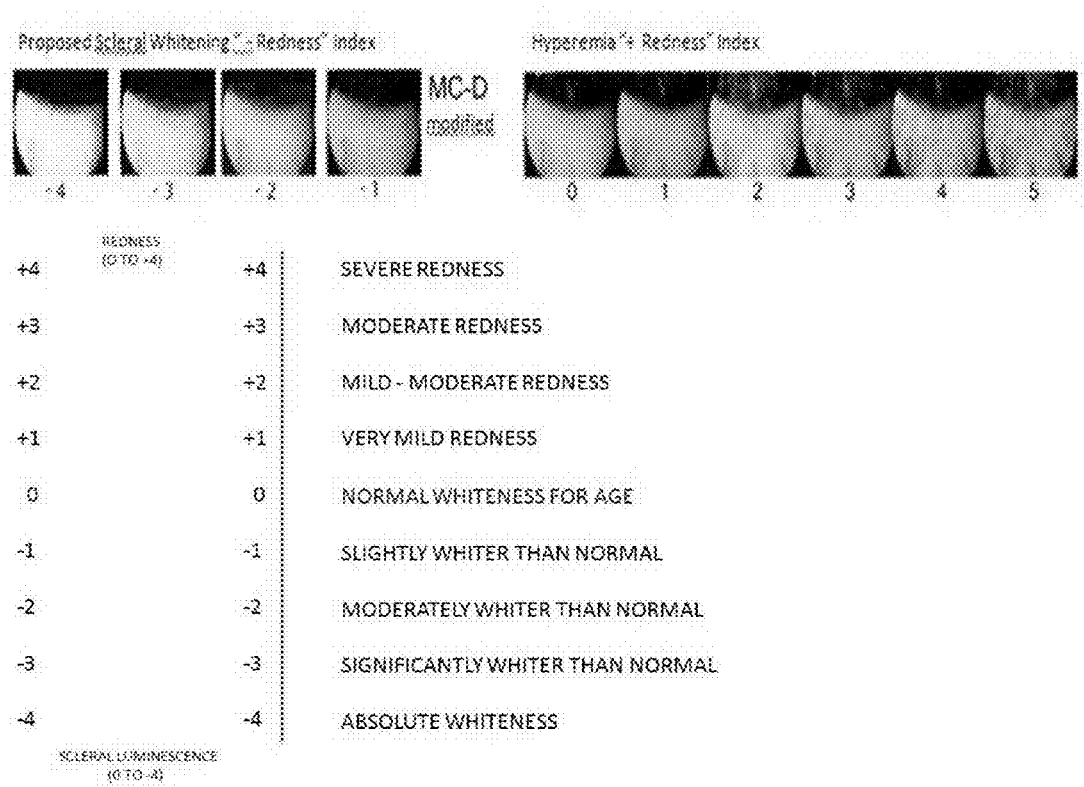
FIG. 5 is a visual representation of the "redness" scale of the invention.
Figure 6A:
FIG. 6A is a photograph of an eye of a subject prior to administration of 0.025% brimonidine.
Figure 6B:
FIG. 6B is a photograph of the same eye as in FIG. 6A after administration of 0.025% brimonidine.
Figure 7:
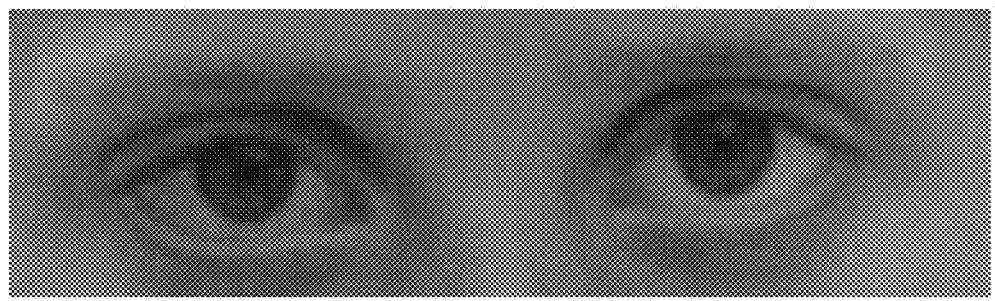
FIG. 7 is a photograph of an eye of a child patient after administration of 0.025% brimonidine.

FIG. 5 illustrates the new scale according to the present invention which allows one to quantify sclera color beyond removal of hyperemia FIGS. 6-14B are explained in the Examples.

The following Examples are provided solely for illustrative purposes and are not meant to limit the invention in any way.

EXAMPLES

Example 1

Effect of Brimonidine on Increasing Whiteness of an Eye

A patient with glaucoma who was receiving Lumigan® (bimatoprost ophthalmic solution 0.03%; a trademark of Allergan, Inc.), treatment, was administered 0.025% brimonidine to reduce redness and increase whiteness of an eye. FIG. 9A is a photograph of the eye prior to administration of 0.025% brimonidine. FIG. 9B is a photograph of the same eye after administration of 0.025% brimonidine.

This Example demonstrates that 0.025% brimonidine resulted in significant reduction of redness and increase of whiteness of an eye.

Example 2

Effect of Brimonidine on Increasing Whiteness of an Eye

Figure 10:
FIG. 10 is a photograph of eyes of a subject, 0.025% brimonidine was administered into the right eye; the left eye is control.

A child patient was administered 0.025% brimonidine to reduce redness and increase whiteness of an eye. FIG. 10 is a photograph of the eye after administration of 0.025% brimonidine.

This Example demonstrates that 0.025% brimonidine resulted in significant reduction of redness and increase of whiteness of an eye.

Example 3

Effect of Brimonidine on Increasing Whiteness of an Eye and Nasal Decongestion

Eight (8) human subjects were administered 0.025% brimonidine. The subjects were administered with the drug in one eye and then asked to assess themselves in the mirror to see if they perceived a difference in conjunctival hyperemia between eyes. The assessments were made 5 minutes after the administration and 4 hours after the administration. After the four hours assessment, the drug was re-administered.

The results of the experiment are as follows. At the initial 5 min assessment, eight of eight subjects reported reduced hyperemia and increased whiteness in the eye to which brimonidine was administered. At the four hour assessment, eight of eight subjects reported reduced hyperemia and increased whiteness in the eye to which brimonidine was administered. Also, at the four hour assessment, six of eight subjects reported reduced nasal congestion in the nostril on the same side as the eye into which the drug was administered.

Photographs of the subjects' eyes were taken 5 minutes after the re-administration of brimonidine at 4 hours after the initial administration.

Figure 8:
FIG. 8 is a photograph of eyes of a subject, 0.025% brimonidine was administered into the left eye; the right eye is control.
Figure 9:
FIG. 9 is a photograph of eyes of a subject, 0.025% brimonidine was administered into both eyes.
Figure 11A:
FIG. 11A is a baseline photograph of eyes of a subject prior to administration of 0.025% brimonidine into the right eye.
Figure 11B:
FIG. 11B is a photograph of eyes of the same subject as in FIG. 11A; 0.025% brimonidine was administered into the right eye; the left eye is control.
Figure 12:
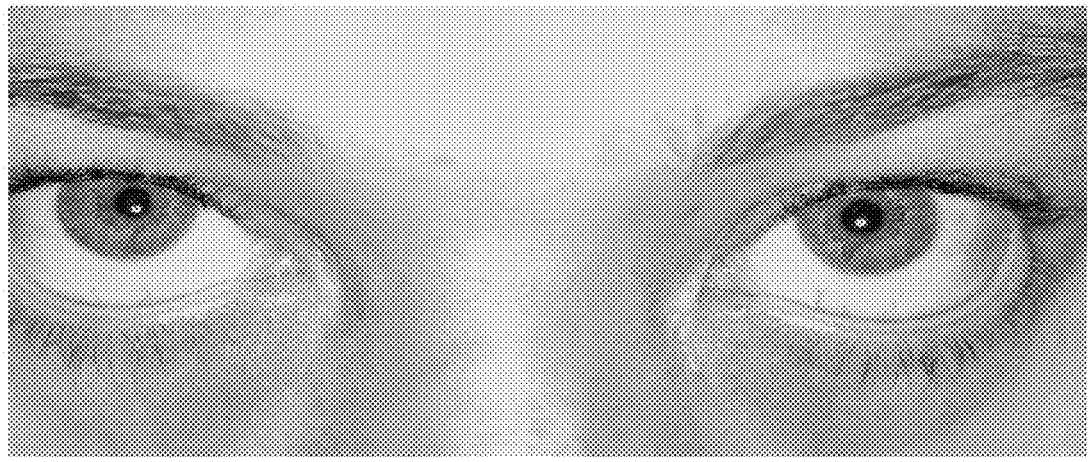
FIG. 12 is a photograph of eyes of a subject, 0.025% brimonidine was administered into the right eye; the left eye is control.

FIG. 8 is a photograph of subject #1, the drug was administered into the left eye; the right eye is control;

FIG. 9 is a photograph of subject #2, the drug was administered into both eyes;

FIG. 10 is a photograph of subject #3, the drug was administered into the right eye; the left eye is control;

FIG. 11A is a photograph of subject #4, the photograph is the baseline and was taken prior to administration of the drug;

FIG. 11B is a photograph of subject #4, the drug was administered into the right eye; the left eye is control; and FIG. 12 is a photograph of subject #5, the drug was administered into the right eye; the left eye is control.

As this Example demonstrates, administration of low dose brimonidine resulted in a significant reduction of redness and increase of whiteness of eyes. In addition, in several subjects, administration of brimonidine into the eye resulted in reducing nasal congestion in the nostril on the same side as the eye into which the drug was administered.

Example 4

Effect of Brimonidine on Increasing of Cosmetic Whiteness of an Eye

Figure 13:
FIG. 13 is a photograph of eyes of a subject prior to administration of 0.025% brimonidine into the right eye.
Figure 14A:
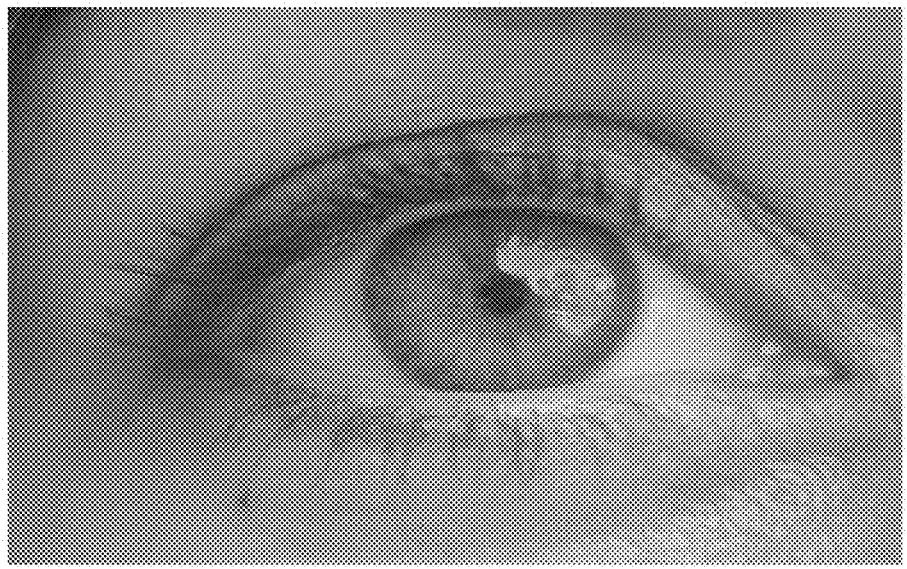
FIG. 14A is a photograph of the right eye of the same subject as in FIG. 13; after 0.025% brimonidine was administered into the right eye.
Figure 14B:
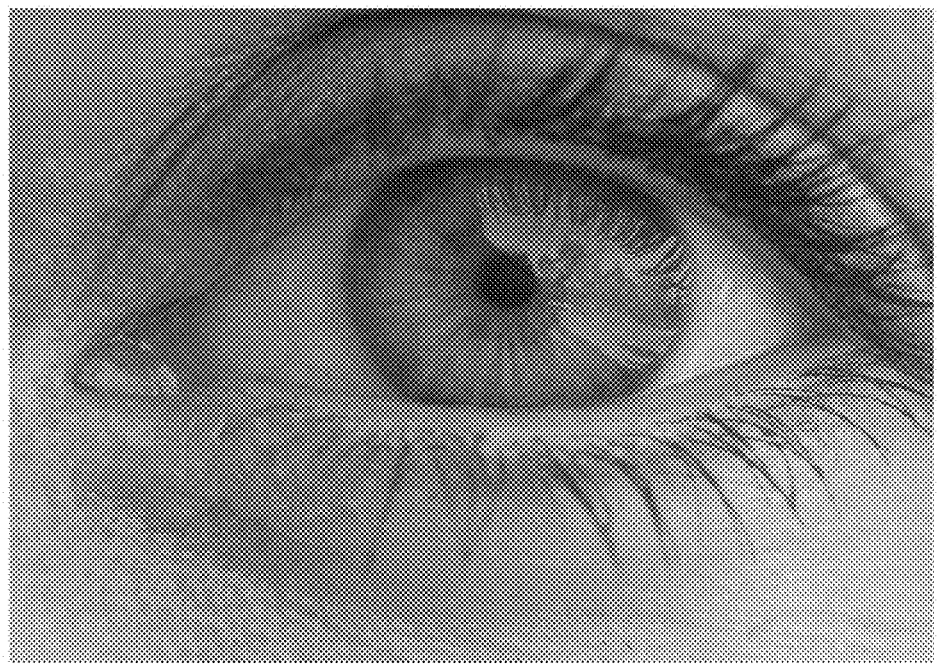
FIG. 14B is a photograph of the left eye of the same subject as in FIG. 13; no brimonidine was administered into the left eye.

A 40-year-old woman with healthy eyes was administered 1gtt (drop per minute) of 0.025% brimonidine into the right eye for three minutes. FIG. 13 is a photograph of both eyes of the woman before the drug was administered. FIG. 14A is a close-up photograph of the right eye and FIG. 14B is a close-up photograph of the left eye.

This Example demonstrates that the right eye was noticeably cosmetically whitened after administration of 0.025% brimonidine.

What is claimed is:

1. A method of increasing whiteness of an eye comprising administering to a subject in need thereof a composition comprising from between about 0.001% to about 0.05% weight by volume of a selective α-2 adrenergic receptor agonist selected from lofexidine, apraclonidine, mivazerol, clonidine, brimonidine, alpha methyl dopa, guanfacine, dexmedetomidine, (+)-(S)-4-[1-(2,3-dimethyl-phenyl)-ethyl]-1,3-dihydro-imidazole-2-thione, and 1-[(imidazolidin-2-yl)imino]indazole, or a pharmaceutically acceptable salt thereof.

2. The method of claim 1, wherein said α-2 adrenergic receptor agonist is brimonidine at a concentration from between about 0.01% to about 0.025% weight by volume.

3. A method of reducing redness of an eye comprising administering to a subject in need thereof a composition comprising from between about 0.001% to about 0.05% weight by volume of a selective α-2 adrenergic receptor agonist selected from lofexidine, apraclonidine, mivazerol, clonidine, brimonidine, alpha methyl dopa, guanfacine, dexmedetomidine, (+)-(S)-4-[1-(2,3-dimethyl-phenyl)-ethyl]-1,3-dihydro-imidazole-2-thione, and 1-[(imidazolidin-2-yl)imino]indazole, or a pharmaceutically acceptable salt thereof.

4. The method of claim 3, wherein said α-2 adrenergic receptor agonist is brimonidine at a concentration from between about 0.01% to about 0.025% weight by volume.

5. A method of reducing redness of an eye while simultaneously increasing whiteness of the eye comprising administering to a subject in need thereof a composition comprising from between about 0.001% to about 0.05% weight by volume of a selective α-2 adrenergic receptor agonist selected from lofexidine, apraclonidine, mivazerol, clonidine, brimonidine, alpha methyl dopa, guanfacine, dexmedetomidine, (+)-(S)-4-[1-(2,3-dimethyl-phenyl)-ethyl]-1,3-dihydro-imidazole-2-thione, and 1-[(imidazolidin-2-yl)imino]indazole, or a pharmaceutically acceptable salt thereof.

6. The method of claim 5, wherein said α-2 adrenergic receptor agonist is brimonidine at a concentration from between about 0.01% to about 0.025% weight by volume.

* * * * *